United States Patent
Kelly et al.

(10) Patent No.: US 11,813,399 B2
(45) Date of Patent: Nov. 14, 2023

(54) CONTINUOUS POSITIVE AIRWAY PRESSURE (CPAP) APPARATUS AND SYSTEM

(71) Applicants: Liauna Kelly, Stockbridge, GA (US); Grace Kirkland, Stockbridge, GA (US)

(72) Inventors: Liauna Kelly, Stockbridge, GA (US); Grace Kirkland, Stockbridge, GA (US)

( * ) Notice: Subject to any disclaimer, the term of this patent is extended or adjusted under 35 U.S.C. 154(b) by 978 days.

(21) Appl. No.: 16/699,040

(22) Filed: Nov. 28, 2019

(65) Prior Publication Data
US 2021/0162152 A1    Jun. 3, 2021

(51) Int. Cl.
*A61M 16/00*    (2006.01)
*A61M 16/06*    (2006.01)

(52) U.S. Cl.
CPC .... *A61M 16/0051* (2013.01); *A61M 16/0003* (2014.02); *A61M 16/06* (2013.01); *A61M 2205/0294* (2013.01); *A61M 2205/581* (2013.01); *A61M 2205/582* (2013.01); *A61M 2210/0618* (2013.01); *A61M 2230/432* (2013.01)

(58) Field of Classification Search
CPC .............. A61M 16/06; A61M 16/0672; A61M 16/085; A61B 5/097
See application file for complete search history.

(56) References Cited

U.S. PATENT DOCUMENTS

| | | | |
|---|---|---|---|
| 6,006,748 A | 12/1999 | Hollis | |
| 6,015,388 A | 1/2000 | Sackner et al. | |
| 6,183,493 B1 | 2/2001 | Zammit | |
| 6,328,753 B1 | 12/2001 | Zammit | |
| 7,059,325 B2 | 6/2006 | Hollis | |
| 7,159,587 B2 | 1/2007 | Drew et al. | |
| 7,322,356 B2 | 1/2008 | Critzer et al. | |
| 7,461,656 B2 | 12/2008 | Gunaratnam et al. | |
| 7,575,553 B2 | 8/2009 | Stahmann et al. | |
| 7,588,033 B2 | 9/2009 | Wondka | |

(Continued)

FOREIGN PATENT DOCUMENTS

| | | |
|---|---|---|
| BR | 8802205 U2 | 6/2010 |
| CN | 201239409 Y | 5/2009 |

(Continued)

*Primary Examiner* — Margaret M Luarca
(74) *Attorney, Agent, or Firm* — Meunier Carlin & Curfman LLC

(57) ABSTRACT

Various implementations include a CPAP alarm system that generates an alarm when the concentration of $CO_2$ is less than a certain threshold. The threshold may represent a minimum concentration of $CO_2$ that is expected to be expelled from the patient. Other implementations are directed to a CPAP apparatus that can couple the CPAP alarm system to a CPAP air delivery device. The CPAP apparatus includes a support body that can be coupled to the CPAP air delivery device and that supports the CPAP alarm system outside of the air delivery device. A $CO_2$ concentration sensor of the CPAP alarm system can be disposed on the apparatus such that the flow of $CO_2$ from a breathing patient is directed toward the $CO_2$ concentration sensor when the CPAP air delivery device is in use and is in the proper position for the patient.

13 Claims, 9 Drawing Sheets

(56) References Cited

U.S. PATENT DOCUMENTS

| | | |
|---|---|---|
| 7,802,571 B2 | 9/2010 | Tehrani |
| 7,845,354 B2 | 12/2010 | Kwok et al. |
| 7,874,293 B2 | 1/2011 | Gunaratnam et al. |
| 7,900,635 B2 | 3/2011 | Gunaratnam et al. |
| 7,926,487 B2 | 4/2011 | Drew et al. |
| 8,042,546 B2 | 10/2011 | Gunaratnam et al. |
| 8,275,553 B2 | 9/2012 | Ochs et al. |
| 8,286,636 B2 | 10/2012 | Gunaratnam et al. |
| 8,353,294 B2 | 1/2013 | Frater et al. |
| 8,381,723 B2 | 2/2013 | Diblasi et al. |
| 8,381,729 B2 | 2/2013 | Freitag et al. |
| 8,398,555 B2 | 3/2013 | Ochs et al. |
| 8,402,972 B2 | 3/2013 | Lang et al. |
| 8,424,530 B2 | 4/2013 | Gunaratnam et al. |
| 8,528,558 B2 | 9/2013 | Drew et al. |
| 8,826,910 B2 | 9/2014 | Kwok et al. |
| 8,833,371 B2 | 9/2014 | Kwok et al. |
| 8,839,791 B2 | 9/2014 | Allum et al. |
| 8,844,529 B2 | 9/2014 | Selvarajan et al. |
| 8,844,533 B2 | 9/2014 | Allum et al. |
| 8,932,227 B2 | 1/2015 | Lynn |
| 8,944,058 B2 | 2/2015 | Ging et al. |
| 8,955,518 B2 | 2/2015 | Wondka |
| 8,997,739 B2 | 4/2015 | Hollis |
| 9,053,222 B2 | 6/2015 | Lynn et al. |
| 9,327,090 B2 | 5/2016 | Steinhauer et al. |
| 9,415,183 B2 | 8/2016 | Allum et al. |
| 9,629,975 B1 | 4/2017 | Pedro et al. |
| 9,770,571 B2 | 9/2017 | Hollis |
| 9,827,391 B2 | 11/2017 | Kwok et al. |
| 9,844,640 B2 | 12/2017 | Darkin et al. |
| 10,058,269 B2 | 8/2018 | Lynn |
| 10,179,217 B2 | 1/2019 | Steinhauer et al. |
| 10,231,864 B1 | 3/2019 | Webster et al. |
| 10,252,016 B2 | 4/2019 | Pedro et al. |
| 2005/0166923 A1 | 8/2005 | Hollis |
| 2006/0196509 A1 | 9/2006 | Drew et al. |
| 2007/0131229 A1 | 6/2007 | Madaus et al. |
| 2008/0257349 A1 | 10/2008 | Hedner et al. |
| 2009/0020120 A1 | 1/2009 | Schatzl et al. |
| 2010/0059058 A1 | 3/2010 | Kuo |
| 2010/0147302 A1 | 6/2010 | Selvarajan et al. |
| 2010/0154798 A1 | 6/2010 | Henry et al. |
| 2011/0277771 A1 | 11/2011 | Kwok et al. |
| 2012/0065533 A1 | 3/2012 | Carrillo, Jr. et al. |
| 2012/0330111 A1 | 12/2012 | Borody |
| 2013/0131534 A1 | 5/2013 | Heatherington et al. |
| 2014/0066800 A1* | 3/2014 | Takatori ............... A61B 5/6803 600/543 |
| 2014/0174444 A1 | 6/2014 | Darkin et al. |
| 2014/0366877 A1 | 12/2014 | Selvarajan et al. |
| 2015/0190606 A1 | 7/2015 | Hollis |
| 2016/0166795 A1 | 6/2016 | Belsinger, Jr. et al. |
| 2017/0007795 A1 | 1/2017 | Pedro et al. |
| 2017/0007796 A1 | 1/2017 | Pedro et al. |
| 2017/0173291 A1 | 6/2017 | Pedro et al. |
| 2017/0232222 A1 | 8/2017 | Darkin et al. |
| 2018/0147385 A1 | 5/2018 | Barnes et al. |
| 2018/0193582 A1 | 7/2018 | Pedro et al. |

FOREIGN PATENT DOCUMENTS

| | | |
|---|---|---|
| CN | 108939231 A | 12/2018 |
| JP | 2008073550 A | 4/2008 |
| JP | 2016523663 A | 8/2016 |
| WO | 2018067563 A1 | 4/2018 |
| WO | 2018084721 A1 | 5/2018 |

* cited by examiner

CONTINUOUS POSITIVE AIRWAY PRESSURE (CPAP) APPARATUS AND SYSTEM

BACKGROUND

There are three primary types of sleep apnea: obstructive sleep apnea, central sleep apnea, and complex sleep apnea. Obstructive sleep apnea is a condition that occurs in a patient when the upper airway is blocked repeatedly during sleep. This blockage can limit or completely stop airflow. Central sleep apnea occurs when the brain doesn't signal the muscles to breathe. Complex sleep apnea is a combination of obstructive sleep apnea and central sleep apnea. Because complex and obstructive sleep apnea both disturb a patient's sleep due to independent causes, complex sleep apnea can disrupt a patient's sleep hundreds of times during a night. Such disruptions significantly fragment a patient's sleep. A patient that has sleep apnea must undergo a sleep study to obtain a diagnosis for which type of sleep apnea the patient has. Sleep apnea testing can be conducted by a doctor or by the patient.

Patients with certain previous medical conditions such as congestive heart failure, type-two diabetes, previous history with strokes, or pulmonary hypertension are usually carefully monitored by doctors for sleep apnea. Such patients may also require different treatment than other sleep apnea patients.

Sleep apnea patients can be tested via a home study or in a laboratory. Although patients may be more comfortable in their own homes, some doctors remain concerned about the accuracy and reliability of home tests.

Obstructive sleep apnea is a common chronic disorder that often requires lifelong care. The most common treatment for obstructive sleep apnea is use of a Continuous Positive Airway Pressure machine, more commonly known as a CPAP. The machine helps obstructive sleep apnea patients breathe more easily during sleep. The CPAP adds additional air pressure to a patient's throat passage to keep the throat passage from collapsing and obstructing the patient's breathing. Most CPAP machines operate by blowing air into a patient's throat at a pressure that gradually increases throughout operation. As the patient sleeps, the air from the CPAP machine continues to hold open the patient's airway to ensure that the patient has unobstructed breathing. It is important that the mask disposed on the patient's face to deliver air from the CPAP machine remain in position to supply a continuous flow of air to the patient.

SUMMARY

Various implementations include a CPAP alarm system for use with a CPAP air delivery device (e.g., a full mask covering the nostrils and mouth, mouthpiece, nasal pillow, or nasal mask) that includes a $CO_2$ concentration sensor and alarm generator to notify a patient if the CPAP air delivery device has fallen off, which is beneficial for the treatment of sleep apnea using a CPAP machine. Various other implementations include a CPAP apparatus for use with the CPAP air delivery device that includes a support body, a sensor frame coupled to one end of the support body, and an air delivery device frame that is coupled to the other end of the support body and can be further coupled to the air delivery device such that the sensor frame is aligned with at least one of the patient's airways when the air delivery device is properly positioned on the patient or is aligned with an outlet of the air delivery device.

Various implementations include a CPAP apparatus comprising a support body, an air delivery device frame, and a sensor frame. The air delivery device frame is coupled to the support body, and the air delivery device frame is couplable to an air delivery device for providing air to a patient. The sensor frame is coupled to and extends from the support body. The sensor frame is spaced apart from the air delivery device frame on the support body, and the sensor frame is disposable externally of the air delivery device. The sensor frame is couplable to a $CO_2$ concentration sensor and aligns the $CO_2$ concentration sensor with at least one of the patient's air passages and/or an exhalation passage from the air delivery device when the CPAP apparatus is in an intended position relative to at least one of the patient's air passages.

In some implementations, the apparatus further includes a $CO_2$ concentration sensor coupled to the sensor frame.

In some implementations, the air delivery device frame is coupled to a nasal mask.

In some implementations, the apparatus further includes a nasal mask coupled to the air delivery device frame, the nasal mask defining at least one recessed portion or at least one post that engages the other of at least one post or at least one recessed portion of the air delivery device frame. For example, in some implementations, the nasal mask defines the at least one recessed portion, and the air delivery device frame comprises the at least one post.

In some implementations, the nasal mask defines a fluid channel, and the fluid channel extends between at least one of the patient's air passages and a $CO_2$ concentration sensor coupled to the sensor frame when the nasal mask is in the intended position adjacent the patient's nose.

In some implementations, the nasal mask includes a partially toroidal shaped body having a first end and a second end. The body also has a radially inward facing surface and a radially outward facing surface. The radially inward facing surface defines an opening configured for being disposed adjacent the patient's nasal openings, and the radially outward facing surface defines an exhalation port. Each of the first and second ends define openings that are in fluid communication with the opening defined by the radially inward facing surface, the exhalation port, and a channel that extends between the first and second ends of the nasal mask. The openings defined by the first and second end are couplable to an air supply source, and exhalation through the patient's nose passes through the exhalation port. The nasal mask defines the at least one recessed portion on an outwardly facing surface of the body of the nasal mask, and the at least one recessed portion is configured for receiving the at least one post of the air delivery device frame for at least partially coupling the air delivery device frame to the nasal mask. For example, in some implementations, the post is disposed within the recessed portion and an adhesive is disposed around the post and the recessed portion.

Other various implementations include a CPAP system that includes a support body, an air delivery device frame coupled to the support body, a sensor frame, a $CO_2$ concentration sensor, and a processor. The air delivery device frame is couplable to an air delivery device. The sensor frame extends from the support body and is spaced apart from the air delivery device frame. The $CO_2$ concentration sensor is coupled to the sensor frame. And, the processor is electrically coupled to the $CO_2$ concentration sensor and a memory. The memory has computer-executable instructions stored thereon that, when executed by the processor, cause the processor to: receive a $CO_2$ concentration signal from the $CO_2$ concentration sensor corresponding to a $CO_2$ concentration in a gas exhaled by the patient, determine, based on the $CO_2$ concentration signal, if the $CO_2$ concentration received by the $CO_2$ concentration sensor is less than a minimum threshold of $CO_2$ concentration expected for the gas exhaled, and generate an alarm signal in response to the $CO_2$ concentration being less than the minimum threshold of $CO_2$ concentration. The $CO_2$ concentration sensor is aligned with the at least one of the patient's air passages when the air delivery device is in an intended position relative to at least one of the patient's air passages.

In some implementations, the CPAP system further includes a power source electrically coupled to the processor.

In some implementations, the CPAP system further includes an alarm generator. The alarm generator is electrically coupled to the processor and generates an alarm in response to receiving the alarm signal from the processor.

In some implementations, the alarm generator is a piezo-buzzer, an audible alarm, and/or a haptic actuator.

In some implementations, the alarm generator generates an alarm at a predetermined time interval after the $CO_2$ concentration detected by the $CO_2$ concentration sensor falls below the threshold.

In some implementations, the predetermined time interval is five seconds.

In some implementations, the CPAP system further includes a nasal mask coupled to the air delivery device frame. The nasal mask defines at least one recessed portion or at least one post that engages the other of at least one post or at least one recessed portion of the air delivery device frame. For example, in some implementations, the nasal mask defines the at least one recessed portion, and the air delivery device frame comprises the at least one post for engaging the recessed portion.

In some implementations, the nasal mask includes a partially toroidal shaped body that has a radially inward facing surface and a radially outward facing surface. The radially inward facing surface defines an opening configured for being disposed adjacent the patient's nasal openings, and the radially outward facing surface defines an exhalation port. The body also includes a first end and a second end. Each of the first and second ends define openings that are in fluid communication with the opening defined by the radially inward facing surface, the exhalation port, and a channel that extends between the first and second ends of the nasal mask. The openings defined by the first and second end are couplable to an air supply source, and exhalation through the patient's nose passes through the exhalation port. And, the nasal mask defines the at least one recessed portion on an outwardly facing surface of the body of the nasal mask, the at least one recessed portion configured for receiving the at least one post of the air delivery device frame for at least partially coupling the air delivery device frame to the nasal mask.

In some implementations, the CPAP system includes at least one air supply tube. One end of the at least one air supply tube is coupled to the opening of the first end or the second end of the nasal mask, and the other end of the at least one air supply tube is coupled to an air source.

Various other implementations include a CPAP $CO_2$ concentration sensor system that includes a processor electrically coupled to a memory, a $CO_2$ concentration sensor couplable to an air delivery device and electrically coupled to the processor, a power source electrically coupled to the processor, and an alarm generator electrically coupled to the processor. The memory has computer-executable instructions stored thereon that, when executed by the processor, cause the processor to: (1) receive a $CO_2$ concentration signal from the $CO_2$ concentration sensor corresponding to a $CO_2$ concentration in a gas exhaled, (2) determine, based on the $CO_2$ concentration signal, if the $CO_2$ concentration received by the $CO_2$ concentration sensor is less than a minimum threshold of $CO_2$ concentration expected for the gas exhaled, and (3) generate an alarm signal in response to the $CO_2$ concentration being less than the minimum threshold of $CO_2$ concentration. The alarm generator receives the alarm signal and generates an alarm.

BRIEF DESCRIPTION OF THE DRAWINGS

Example features and implementations are disclosed in the accompanying drawings. However, the present disclosure is not limited to the precise arrangements and instrumentalities shown.

DETAILED DESCRIPTION

The devices, systems, and methods disclosed herein provide for a CPAP alarm system that generates an alarm when the concentration of $CO_2$ is less than a certain threshold. The threshold may represent a minimum concentration of $CO_2$ that is expected to be expelled from the patient. This low concentration condition may occur when the apparatus is not mounted in an expected position relative to a patient's mouth and/or when the patient's breathing has slowed, stopped, or is obstructed. The $CO_2$ concentration is measured by a $CO_2$ concentration sensor. The CPAP alarm system includes a $CO_2$ concentration sensor and an alarm generator.

A CPAP apparatus couples the CPAP alarm system to a CPAP air delivery device. The CPAP air delivery device facilitates the flow of air from the air supply, such as a CPAP machine, into the patient's mouth. The CPAP apparatus includes a support body that can be coupled to the CPAP air delivery device. A portion of the support body that is external to the air delivery device is coupled to a sensor frame, and the $CO_2$ concentration sensor can be coupled to the sensor frame. The $CO_2$ concentration sensor is disposed on the apparatus such that the flow of $CO_2$ from a breathing patient is directed toward the $CO_2$ concentration sensor when the CPAP air delivery device is in use and is in the proper position for the patient. In some implementations, the support body is elongated and defines a channel through it. For example, as shown in FIGS. 1A-1C, the support body is cylindrical.

In response to the $CO_2$ concentration being below the minimum concentration threshold, an alarm is generated by the alarm generator, and the patient can re-secure the CPAP air delivery device to continue treatment of sleep apnea. A significant problem that sleep apnea patients experience with current CPAP systems is that the mask that delivers air to the patient sometimes moves out of the proper position or falls away from the patient's face while the patient is sleeping.

Figure 1A:
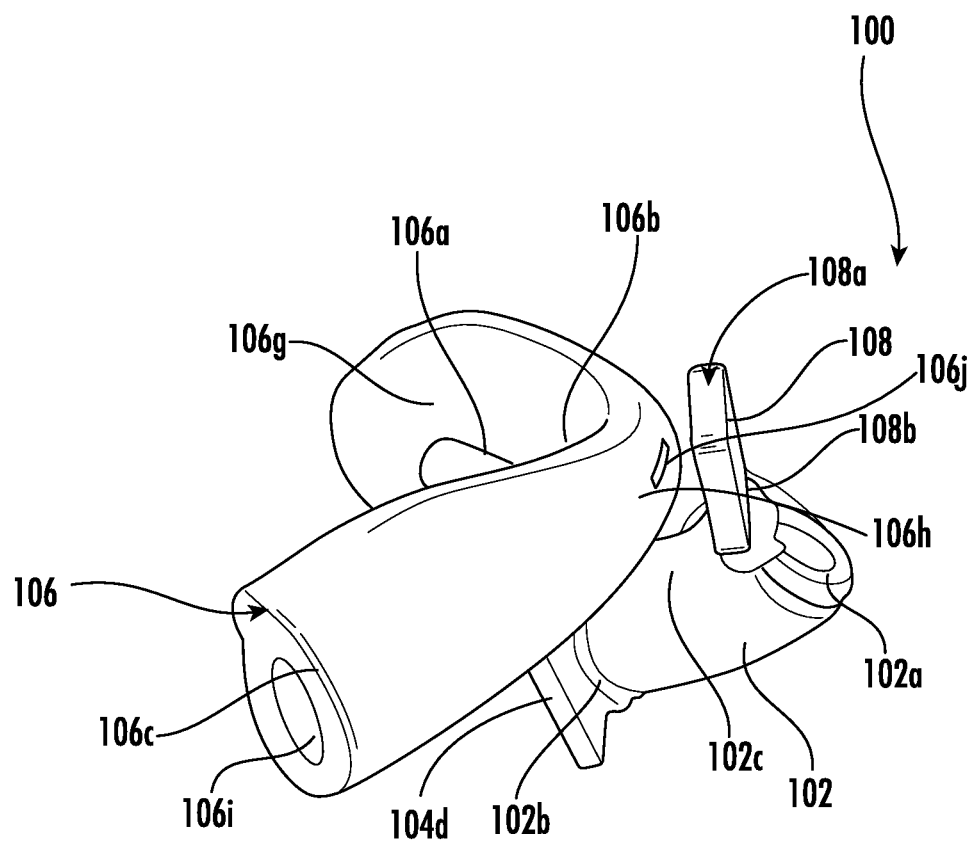
FIGS. 1A-1C are perspective views of a CPAP apparatus coupled with a nasal mask according to one implementation.
Figure 1B:
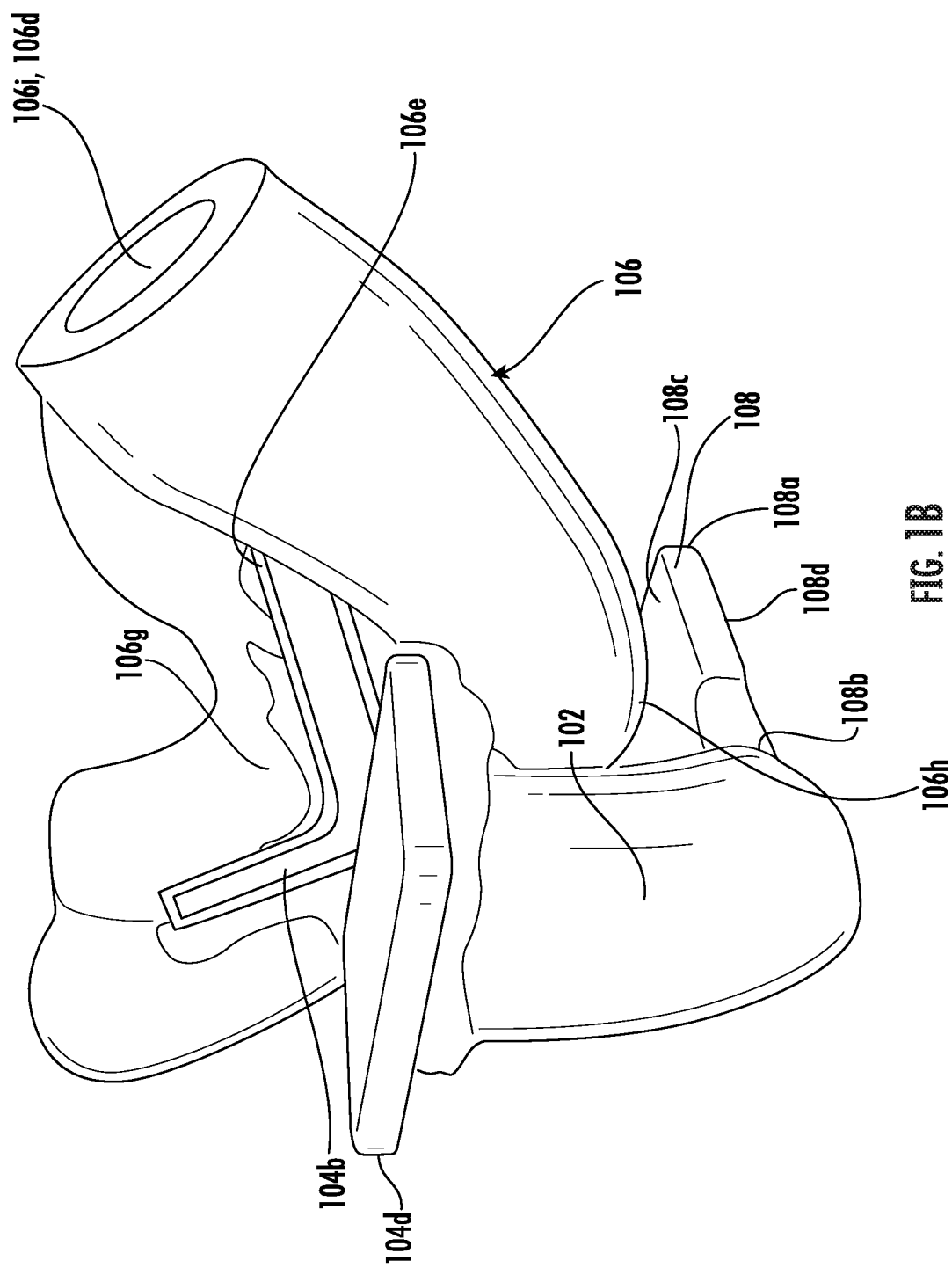
Figure 1C:
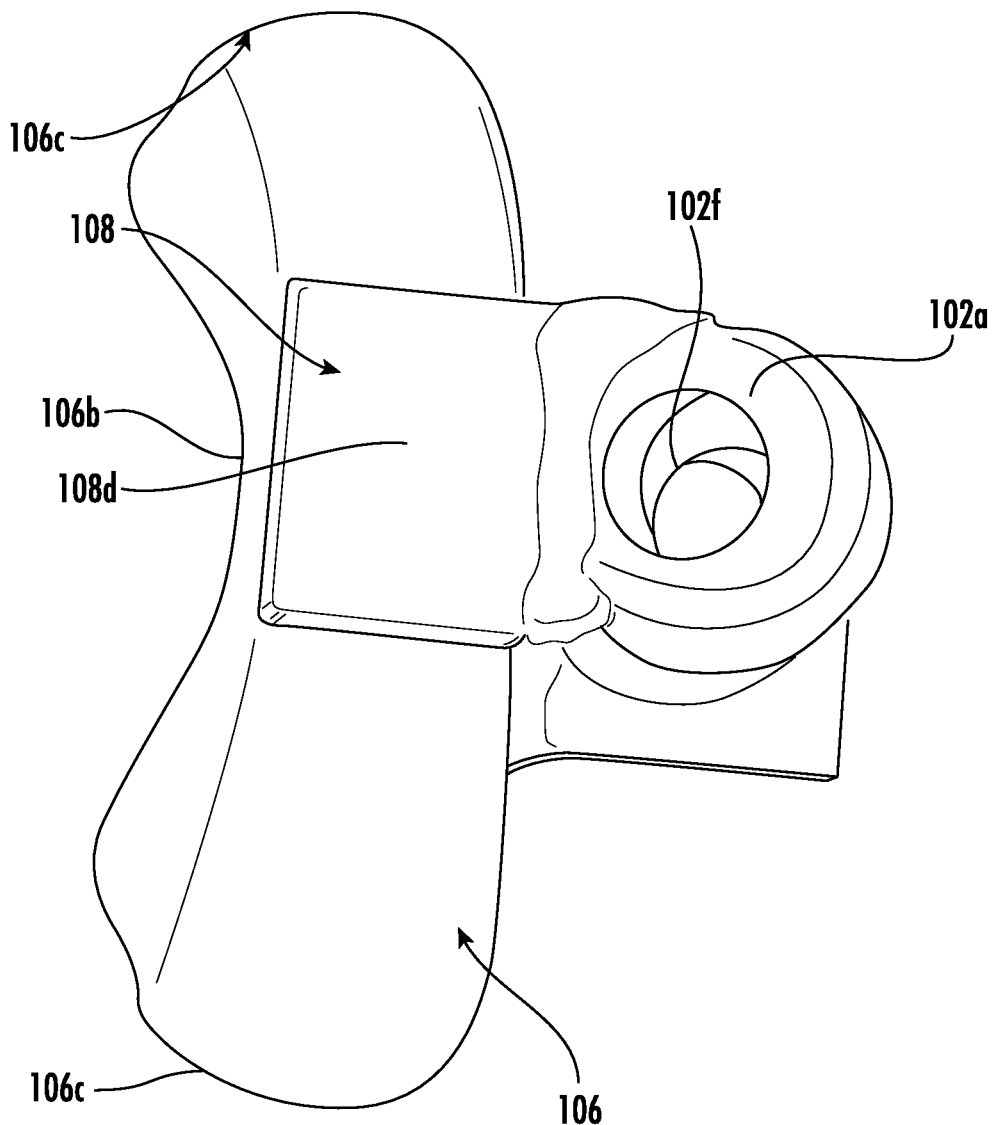

FIG. 1A-C shows a CPAP apparatus 100 and nasal mask 106 as the air delivery device, according to one implementation. The CPAP apparatus 100 has a support body 102, an air delivery device frame 104, and a sensor frame 108. The support body 102 is elongated and has a first end 102a, a second end 102b, and an outer surface 102c that extends between the first end 102a and the second end 102b. The first end 102a is opposite and spaced apart from the second end 102b. The elongated support body 102 is cylindrical shaped in FIGS. 1A-1C.

In the implementation shown in FIGS. 1A-1C, the support body 102 defines a hollow channel 102f extending between the ends 102a, 102b. In some implementations, wires for coupling the sensor to a power source may be extended through the channel 102f. In other implementations, the support body 102 may be solid and not define such a channel.

Although the support body 102 in FIGS. 1A-1C is a cylindrical body, in other implementations, the support body 102 can be a semi-cylindrical shaped body or other suitable elongated shape (e.g., rectangular prism, triangular prism, prismatic shape having an arcuate or straight central longitudinal axis) suitable for supporting the air delivery device frame 104 and the sensor frame 108.

In the implementation shown in FIG. 1, the support body 102 is formed from plastic, but the support body 102 can be formed from any suitable material, such as plastic, silicone, rubber, wood, and/or metal.

Figure 2:
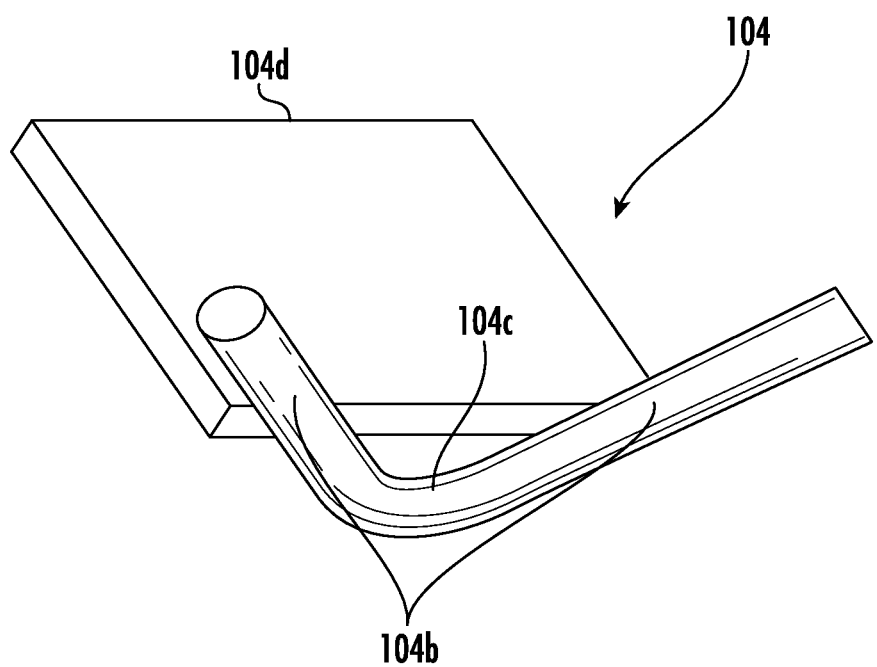
FIG. 2 is a perspective view of the air delivery device frame and support body shown in FIGS. 1A-1C but without the nasal mask.

The air delivery device frame 104 couples the support body 102 and air delivery device. The air delivery device frame 104 includes two posts 104b, a central portion 104c that extends between and couples proximal ends of the two posts 104b, and a plate portion 104d that is coupled to at least a portion of the central portion 104c and/or the posts 104b, as shown in FIGS. 1B and 2. The posts 104b extend in a V-shape (or U-shape) relative to each other. The plate portion 104d is coupled to the second end 102b of the support body 102. In some implementations, at least a portion of the air delivery device frame 104 is integrally formed with the support body 102, and in other implementations, at least a portion of the air delivery device frame 104 is formed separately from the support body 102 and is coupled thereto using a suitable fastener, such as adhesive, welding, clips, or other suitable fastener. In addition, the posts 104b are cylindrically shaped in FIGS. 1B and 2, but in other implementations, the posts may have other suitable elongated shapes. Furthermore, in other implementations, the air delivery device frame 104 may include two posts that are not coupled to the central portion 104c but are directly coupled to the plate 104d or directly to the support body 102.

The sensor frame 108 has a first end 108a and a second end 108b. The second end 108b of the sensor frame 108 is coupled to the support body 102 adjacent the first end 102a of the support body, and the first end 108a of the sensor frame 108 is spaced apart from the support body 102 such that a plane extending between the ends 108a, 108b of the sensor frame 108 is transverse to the central longitudinal axis extending through the support body 102. The plane extending between the ends 108a, 108b of the sensor frame 108 extends radially outwardly from the outer surface 102c of the support body 102.

Figure 3:
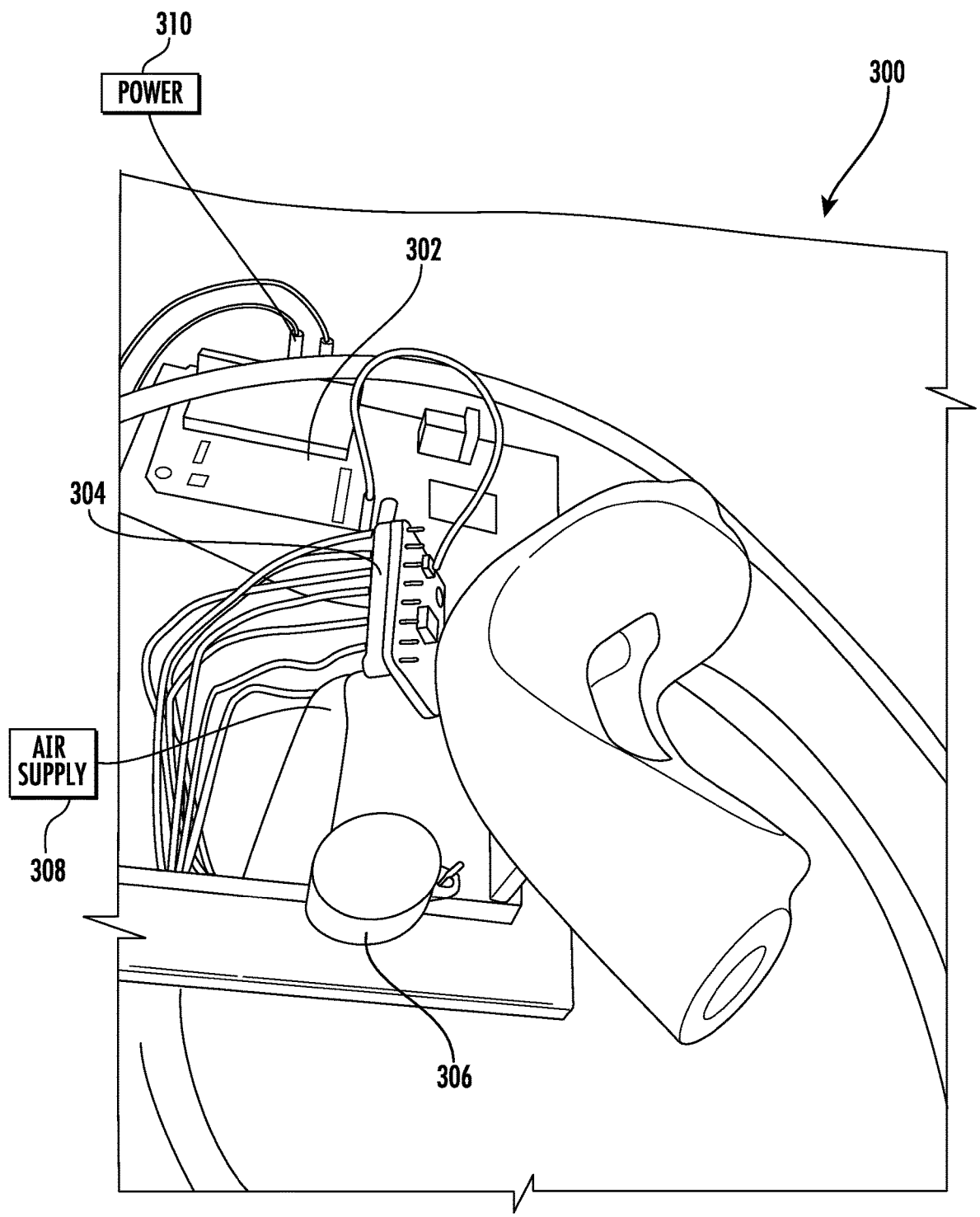
FIG. 3 is a perspective view of a CPAP system according to one implementation that includes the CPAP apparatus shown in FIGS. 1A-1C.

The sensor frame 108 has a first surface 108c and a second surface 108d opposite and spaced apart from the first surface 108c. The surfaces 108c, 108d extend between the first and second ends 108a, 108b. The first surface 108c faces the air delivery device frame 104, and the second surface 108d faces in the opposite direction. A $CO_2$ concentration sensor 304 is coupled to the first surface 108c of the sensor frame 108, which is shown in FIG. 3. For example, the first surface 108c may be planar, and the $CO_2$ concentration sensor 304 may be coupled to the first surface 108c by an adhesive or other suitable fastener, such as, for example, a clip, rivet, or hook and loop. The first surface 108c of the sensor frame 108 is aligned with an exhalation passage of the patient or of the air delivery device when the apparatus 100 is in the proper position.

The air delivery device shown in FIGS. 1A-1C is a nasal mask 106. The nasal mask 106 includes a partially toroidal shaped body having first and second ends 106c. In other words, the nasal mask 106 has an arcuate shape as viewed from a plane that bisects ends 106c and a central portion 106b of the nasal mask 106 as shown in FIG. 1A. The body also includes a radially inward facing surface 106g and a radially outward facing surface 106h. The radially inward facing surface 106g defines an opening 106a configured for being disposed adjacent the patient's nasal openings, and the radially outward facing surface 106h defines an exhalation port 106j. The radially inward facing surface 106g slopes radially inwardly.

Each of the first and second ends 106c define openings 106i that are in fluid communication with the opening 106a defined by the radially inward facing surface 106g, the exhalation port 106j, and a fluid channel that extends through the body along the central longitudinal axis thereof and between the first and second ends 106c of the nasal mask 106. The openings 106i defined by the first and second ends 106c are couplable to an air supply source, and exhalation through the patient's nose passes through the exhalation port 106j. Pressurized air from the air supply source exits through this opening 106a and passes into the patient's nostrils. An example nasal mask includes the Philips DREAMWEAR Under the Nose Nasal Mask (https://www.sleepapnea.com/products/masks/dreamwear/nasal/). Exhaled gas may also pass through the patient's mouth.

A portion of the outer surface of the body of the nasal mask 106 defines at least one recessed portion 106e. In the implementation shown in FIG. 1B, two recessed portions 106e extend along the outer surface from a central portion 106c of the outer surface. The recessed portions 106e shown in FIG. 1B extend along a portion of the outer surface of the body of the nasal mask 106 that is inferior of the nasal opening 106a when worn. However, in other implementations, the recessed portions may be defined on a portion of the outer surface of the body of the nasal mask that is in the superior direction of the nasal opening 106a when worn. A cross sectional shape of the recessed portions 106e as taken through an axis of the recessed portions 106e is semi-cylindrical, and the recessed portions 106e are dimensioned to receive the posts 104b of the air delivery device frame 104 to couple to the air delivery device frame 104 and support the nasal mask 106 relative to the air delivery device frame 104. For example, as shown in FIG. 1B, a width of the recessed portions 106e is the same or smaller than a diameter of the posts 104b such that the posts 104b can be engaged into the recessed portions 106e and held in place via a friction fit. In other implementations, the recessed portion 106e may include one recessed portion that extends from the center. Also, in other implementations, the cross-sectional shape of the recessed portion 106e may have another shape, such as rectangular or other suitable shape, for receiving the posts 104b. The posts 104b may also be held in place within the recessed portion(s) 106e via adhesive or other suitable fastening mechanism.

As noted above, openings 106i are couplable to an air supply source, for example, via air supply tubes that are connected to the pressurized air supply source. Air supply tubes are coupled with the openings 106i via a friction fit. However, in other implementations, the openings 106i may be coupled to the air supply tubes using a threaded engagement, clamp, or other suitable fastening mechanism.

In some implementations, the nasal mask 106 is formed from plastic, rubber, silicone, or any suitable material capable of being secured in a patient's mouth. Although the implementation shown in FIGS. 1A-1C includes a nasal mask, in other implementations, the CPAP air delivery device may be a full mask that covers the nose and mouth, a mouthpiece, or a nasal pillow mask. Example full masks and nasal pillow masks are shown at https://www.sleepapnea.com/products/masks/.

FIG. 3 shows a CPAP system 300, which includes the CPAP apparatus 100, the nasal mask 106, a processor 302, $CO_2$ concentration sensor 304, an alarm generator 306, a pressurized air supply source 308, and a power source 310. The processor 302 is electrically coupled to the $CO_2$ concentration sensor 304, the alarm generator 306, and the power source 310. For example, the processor 302 and the sensor 304 may be electrically coupled to a printed circuit board. The alarm generator 306 may also be electrically coupled to the printed circuit board. Alternatively, other electrical connection systems may be used, such as a breadboard. The processor 302 may also be electrically coupled with other devices used in the CPAP system 300 that are controlled electronically. The processor 302 includes a timer and is electrically coupled to a memory that stores computer-executable instructions that are executable by the processor 302. For example, the processor 302 is an Arduino Microcontroller in the implementation shown in FIG. 3, but in other implementations, it may be another suitable processor. The power source 310 can be a building electrical system, a battery, or any other power source capable of providing electrical power to the processor 302.

When the nasal mask 106 is in the correct position adjacent the patient's nose, the $CO_2$ concentration sensor 304 is aligned with the exhalation opening 106j of the nasal mask 106 such that the sensor 304 is in the path of the patient's exhaled breath. The $CO_2$ concentration sensor 304 generates a signal corresponding to the $CO_2$ concentration in the patient's exhaled breath, and this signal is received by the processor 302. The processor 302 determines, based on the $CO_2$ concentration signal, if the $CO_2$ concentration received by the $CO_2$ concentration sensor is less than a minimum $CO_2$ concentration threshold expected for the patient's exhaled breath. In response to the measured $CO_2$ concentration being less than the minimum threshold of the $CO_2$ concentration, the processor 302 generates an alarm signal and sends the alarm signal to the alarm generator 306. A drop in $CO_2$ concentration may result when a patient's breathing is interrupted and the flow of exhaled air from the patient's air passages is no longer steady or discharged at a steady pace. For example, this may occur when the nasal mask 106 shifts away from the correct position adjacent the patient's nostrils. In some implementations, the minimum $CO_2$ concentration threshold is 600 ppm (e.g., below 400 ppm).

In some implementations, the processor 302 waits a predetermined time interval after determining that the $CO_2$ concentration measured is below the minimum $CO_2$ concentration threshold to avoid a false alarm. For example, the predetermined time interval may be five seconds. In other implementations, the predetermined time interval may be less than 5 seconds or more than 5 seconds.

The alarm signal generated by the processor 302 is received by the alarm generator 306. In some implementations, the alarm generator may include an audible alarm, a piezo buzzer, and/or a haptic actuator (e.g., eccentric rotating mass motor or a linear resonance actuator). In some implementations the alarm generator 306 is a Mallory 539-PK21N30WQ piezo buzzer. The alarm generator 306 generates an alarm that is sufficiently loud and/or has sufficient vibration to wake an average sleeping patient. In some implementations, the processor 302 may also communicate the alarm signal to an electronic computing device that is located remotely from the apparatus 100. In some implementations, the processor 302 transmits the alarm signal to the alarm generator 306 through a wired network and/or a wireless network, such as, Bluetooth, WIFI, ZigBee, or any form of wireless communication capable of transmitting a signal. The alarm generator 306 may be disposed on the CPAP apparatus 100, on the air delivery device, or provided separately from the CPAP apparatus 100 and the air delivery device. In some implementations, the remote computing device is a cellular phone (e.g., smartphone), tablet, or laptop.

FIG. 8 illustrates an example computer. $CO_2$ concentration sensor 304, processor 302, and alarm generator 306, as well as other system components, can be implemented with all or some of the components shown in FIG. 8.

The computer may include one or more hardware components such as, for example, a central processing unit (CPU) 821, a random-access memory (RAM) module 822, a read-only memory (ROM) module 823, a storage 824, a database 825, one or more input/output (I/O) devices 826, and an interface 827. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 824 may include a software partition associated with one or more other hardware components. It is understood that the components listed above are exemplary only and not intended to be limiting.

CPU 821 may include one or more processors, each configured to execute instructions and process data to perform one or more functions associated with a computer for monitoring water treatment and flow. CPU 821 may be communicatively coupled to RAM 822, ROM 823, storage 824, database 825, I/O devices 826, and interface 827. CPU 821 may be configured to execute sequences of computer program instructions to perform various processes. The computer program instructions may be loaded into RAM 822 for execution by CPU 821.

RAM 822 and ROM 823 may each include one or more devices for storing information associated with operation of CPU 821. For example, ROM 823 may include a memory device configured to access and store information associated with the computer, including information for identifying, initializing, and monitoring the operation of one or more components and subsystems. RAM 822 may include a memory device for storing data associated with one or more operations of CPU 821. For example, ROM 823 may load instructions into RAM 822 for execution by CPU 821.

Storage 824 may include any type of mass storage device configured to store information that CPU 821 may need to perform processes consistent with the disclosed embodiments. For example, storage 824 may include one or more magnetic and/or optical disk devices, such as hard drives, CD-ROMs, DVD-ROMs, or any other type of mass media device.

Database 825 may include one or more software and/or hardware components that cooperate to store, organize, sort, filter, and/or arrange data used by CPU 821. For example, database 825 may store data relating to monitoring water treatment and flows, associated metadata, and health information. It is contemplated that database 825 may store additional and/or different information than that listed above.

I/O devices 826 may include one or more components configured to communicate information with a user associated with the device shown in FIG. 8. For example, I/O devices 826 may include a console with an integrated keyboard and mouse to allow a user to maintain a historical database of information, update associations, and access digital content. I/O devices 826 may also include a display including a graphical user interface (GUI) for outputting information on a monitor. I/O devices 826 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 827 may include one or more components configured to transmit and receive data via a communication network, such as the Internet, a local area network, a workstation peer-to-peer network, a direct link network, a wireless network, or any other suitable communication platform. For example, interface 827 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object-oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices.

These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

Various other examples and methods are described herein.

The researchers considered whether to include $CO_2$ concentration sensors within masks of existing CPAP systems, but the researchers were concerned that the higher humidity levels within the mask could damage the sensor. In addition, the interior portion of existing masks may not be large enough to accommodate a sensor. Thus, the researchers determined that having a support body coupled to a sensor frame that is disposed outside of the mask would reduce the risk of sensor damage from humidity and would avoid space constraints within the mask.

The researchers produced the apparatus 100 described above using 3D printing, which is also known as additive manufacturing. In the additive manufacturing process, thin layers of material are laid horizontally and stacked on top of each other until the desired object is formed. The researchers created a digital file of the object to be printed using a 3D design program, such as Google SketchUp or other suitable 3D design program.

Figure 4:
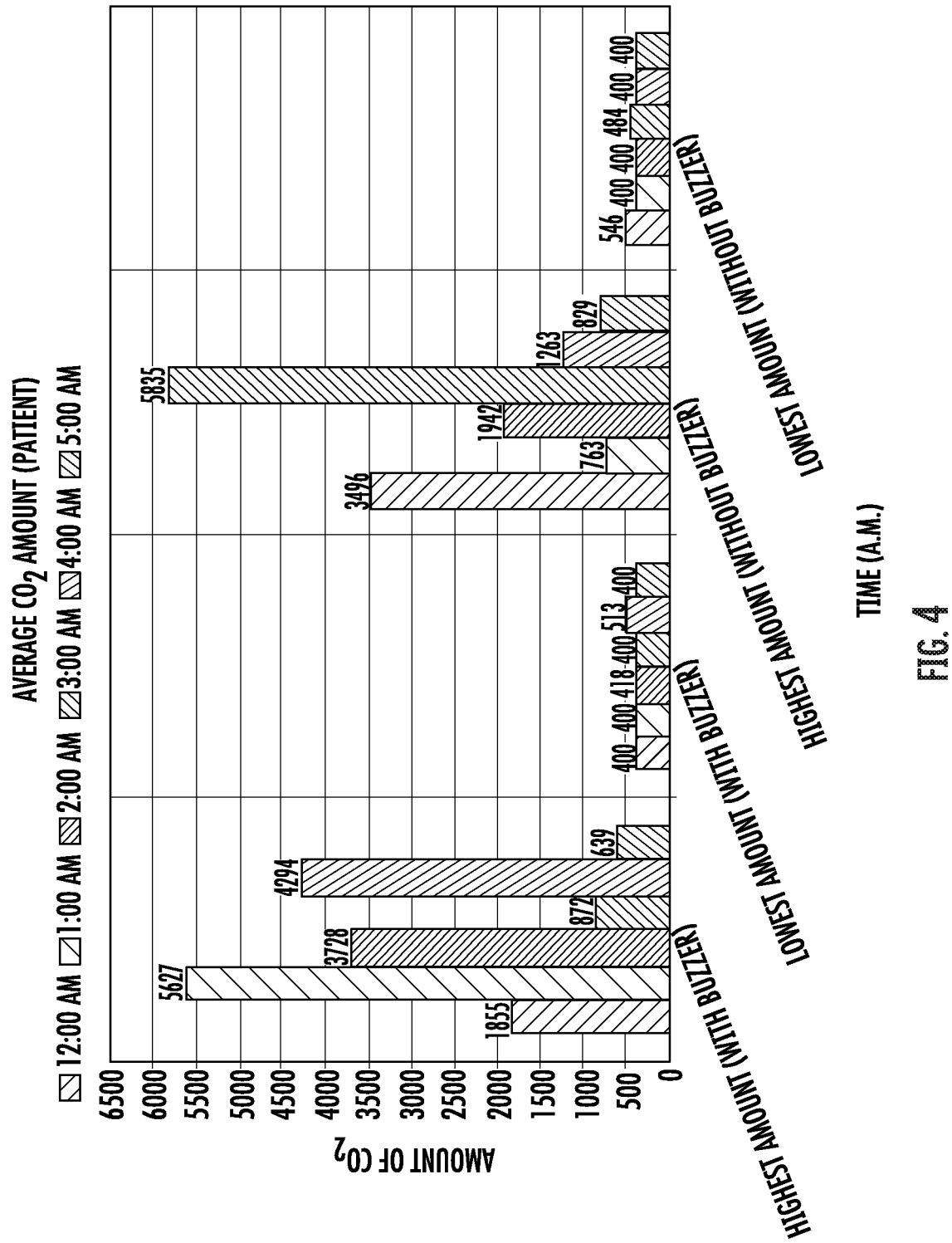
FIG. 4 shows results from a test measuring the highest and lowest $CO_2$ concentrations of a test patient using the air delivery device and CPAP apparatus in FIGS. 1A-1C with and without an alarm generator coupled thereto at different times during the night.

The researchers tested the prototypes. FIG. 4 shows the results of a test measuring the highest and lowest $CO_2$ concentrations of a test patient using apparatus 100 with and without an alarm generator 306 coupled thereto at different times during the night. The alarm generator used in this experiment was a buzzer. The average lowest concentration for the apparatus 100 with the buzzer was lower than the average lowest concentration for the apparatus 100 without the buzzer. Thus, the apparatus 100 that included the buzzer alerted the patient to adjust the position of the air delivery device more quickly.

Figure 5:
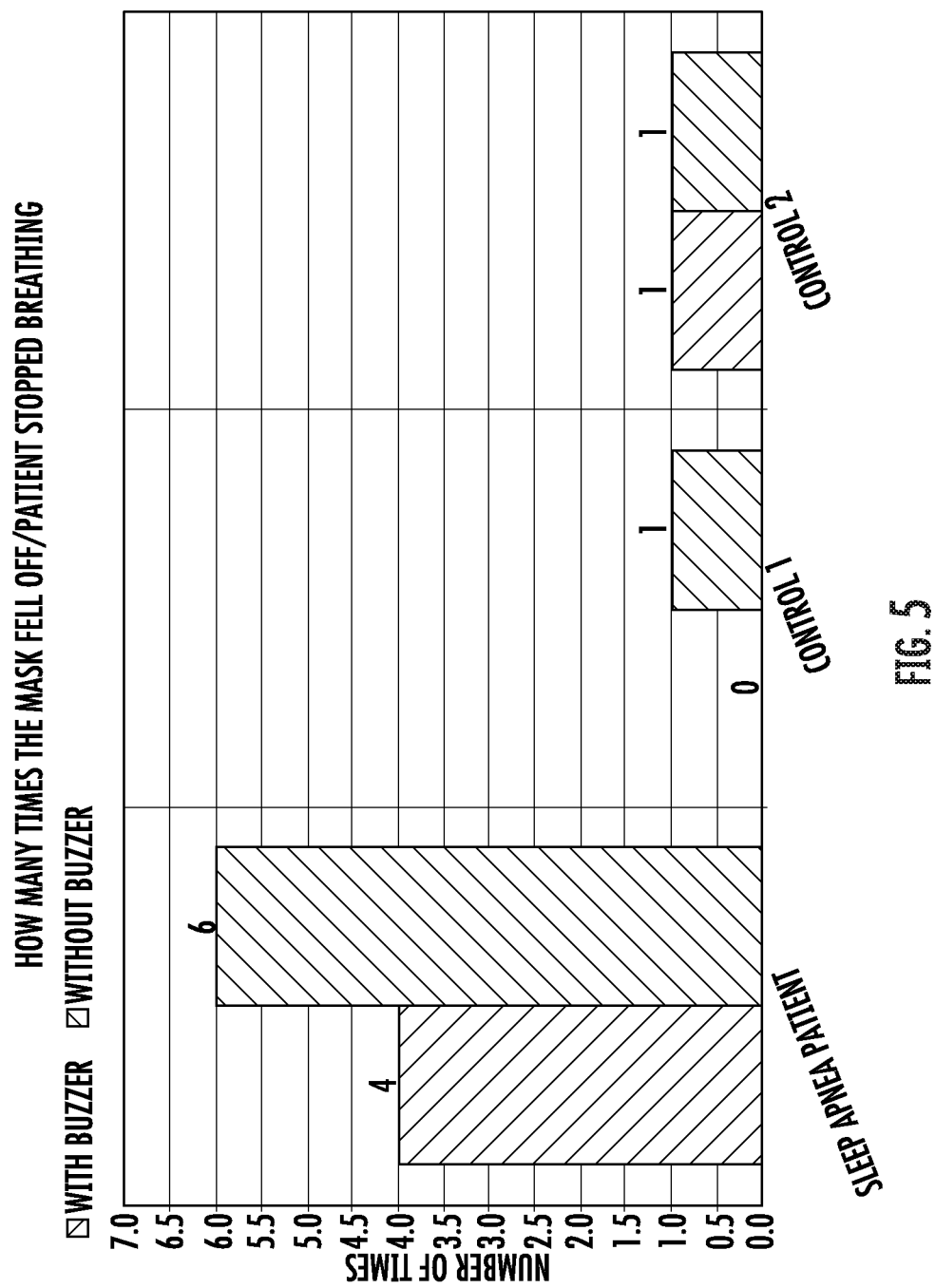
FIG. 5 shows the number of times the air delivery device and CPAP apparatus in FIGS. 1A-1C with and without the alarm generator shifted from the proper position or the patients stopped breathing when the patients were using the air delivery device and CPAP apparatus.

FIG. 5 shows a chart illustrating the number of times the air delivery device shifted from the proper position or the patient stopped breathing for a sleep apnea patient as compared with two control patients that do not have sleep apnea. The experiment compared the data for an air delivery device coupled with the apparatus 100 with and without the buzzer. For the sleep apnea patient and one of the control patients, the air delivery device shifted or the patients stopped breathing more times using the air delivery device and apparatus 100 without the buzzer than when using the air delivery device and apparatus 100 with the buzzer. As shown in FIG. 5, the air delivery device and apparatus 100 with the buzzer fell off of the sleep apnea patient four times, compared to six times when the buzzer was not present. For the control patients, the air delivery device shifted from the proper position once when the apparatus 100 did not have the buzzer. This was because of the size of the air delivery device. And for the second control patient, the air delivery device shifted from the proper position once when the apparatus 100 did have the buzzer, which was also because of the size of the air delivery device. Thus, the buzzer's presence is not correlated with an increased risk that the air delivery device will shift.

Figure 6:
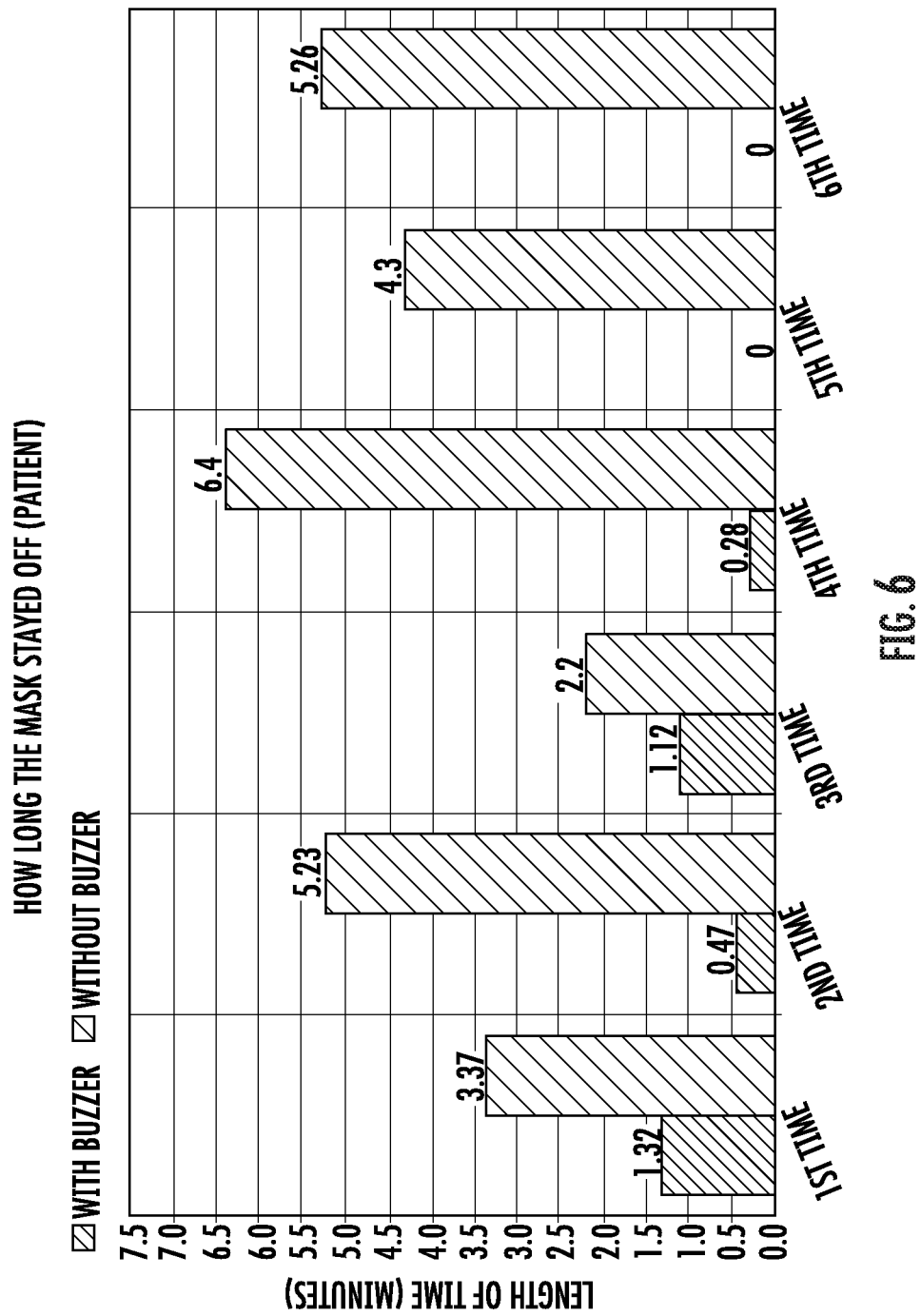
FIG. 6 shows a chart illustrating the comparison of the time that the air delivery device and CPAP apparatus in FIGS. 1A-1C were in the improper position when coupled to the apparatus 100 with and without the buzzer.
Figure 7:
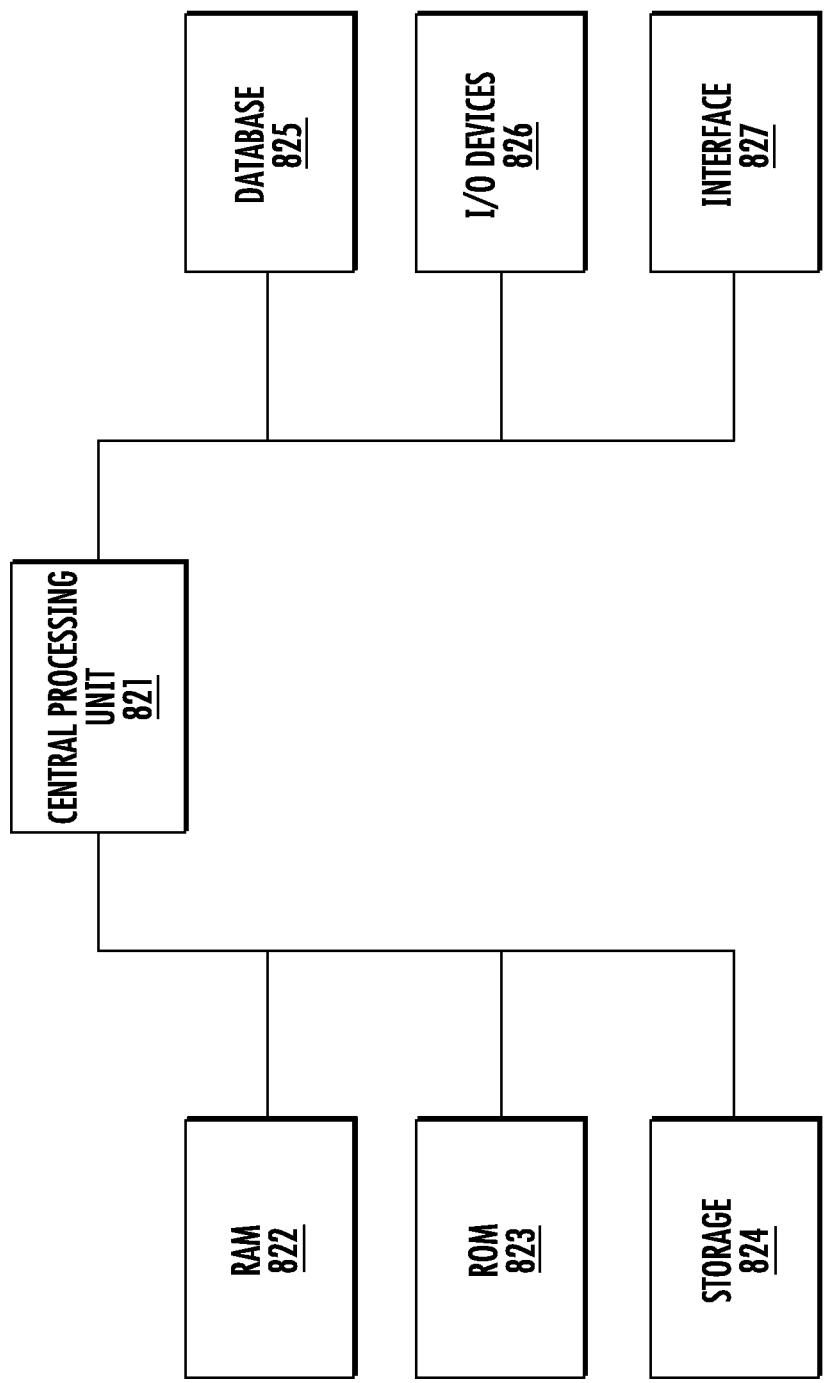
FIG. 7 illustrates an example computer according to aspects of the disclosed implementations.

FIG. 6 shows a chart illustrating a comparison of the time that the air delivery device was in the improper position when coupled to the apparatus 100 with and without the buzzer for the sleep apnea patient. The first time that the air delivery device shifted from the proper position when coupled to the apparatus 100 with the buzzer, it remained in the improper position for 1 minute and 4 seconds. The second time it remained in the improper position for 1 minute and 17 seconds. The third time it remained in the improper position for 1 minute and 20 seconds. The fourth time it remained in the improper position for 58 seconds. The first time that the air delivery device shifted from the proper position when coupled to the apparatus 100 without the buzzer, it remained in the improper position for 1 minutes and 36 seconds. The second time it remained in the improper position for 2 minutes and 54 seconds. The third time it remained in the improper position for 1 minute and 49 seconds. The fourth time it remained in the improper position for 1 minute and 56 seconds. The fifth time it remained in the improper position for 2 minutes and 37 seconds. The final time it remained in the improper position for 2 minutes and 48 seconds. The amount of time the air delivery device was in the improper position when coupled to the apparatus with the buzzer is low compared to the amount of time the device was in the improper position when coupled to the apparatus without the buzzer. Thus, the amount of time it took the patient to reposition the air delivery device with the apparatus 100 with the buzzer was lower compared to the amount of time it took the patient to reposition the air delivery device when coupled to the apparatus without the buzzer.

What is claimed is:

1. A CPAP apparatus comprising:
   a support body;
   an air delivery device frame coupled to the support body, wherein the air delivery device frame is couplable to an air delivery device for providing air to a patient;
   a sensor frame coupled to and extending from the support body, the sensor frame being spaced apart from the air delivery device frame on the support body, and the sensor frame being disposable externally of the air delivery device; and
   a nasal mask coupled to the air delivery device frame, the nasal mask defining at least one recessed portion or at least one post that engages the other of at least one post or at least one recessed portion of the air delivery device frame, the nasal mask further comprising:
      a partially toroidal shaped body having a radially inward facing surface and a radially outward facing surface, the radially inward facing surface defining an opening configured for being disposed adjacent the patient's nasal openings, and the radially outward facing surface defining an exhalation port,
      wherein the partially toroidal body comprises a first end and a second end,
      wherein each of the first and second ends define openings that are in fluid communication with the opening defined by the radially inward facing surface, the exhalation port, and a channel that extends between the first and second ends of the nasal mask;

wherein the openings defined by the first and second end are couplable to an air supply source, and exhalation through the patient's nose passes through the exhalation port; and wherein the nasal mask defines the at least one recessed portion on an outwardly facing surface of the body of the nasal mask, the at least one recessed portion configured for receiving the at least one post of the air delivery device frame for at least partially coupling the air delivery device frame to the nasal mask, wherein the sensor frame is couplable to a $CO_2$ concentration sensor and aligns the $CO_2$ concentration sensor with at least one of the patient's air passages and/or an exhalation passage from the air delivery device when the CPAP apparatus is in an intended position relative to at least one of the patient's air passages.

2. The CPAP apparatus of claim 1, wherein the $CO_2$ concentration sensor is coupled to the sensor frame.

3. The CPAP apparatus of claim 1, wherein the nasal mask defines the at least one recessed portion, and the air delivery device frame comprises the at least one post.

4. The CPAP apparatus of claim 1, wherein the nasal mask defines a fluid channel, and the fluid channel extends between at least one of the patient's air passages and the $CO_2$ concentration sensor coupled to the sensor frame when the nasal mask is in the intended position adjacent the patient's nose.

5. The CPAP apparatus of claim 1, wherein the post is disposed within the recessed portion and an adhesive is disposed around the post and the recessed portion.

6. A CPAP System comprising:
 a support body;
 an air delivery device frame coupled to the support body, wherein the air delivery device frame is couplable to an air delivery device;
 a sensor frame coupled to and extending from the support body and spaced apart from the air delivery device frame on the support body, the sensor frame being disposable externally of the air delivery device;
 a nasal mask coupled to the air delivery device frame, the nasal mask defining at least one recessed portion or at least one post that engages the other of at least one post or at least one recessed portion of the air delivery device frame, the nasal mask further comprising:
  a partially toroidal shaped body having a radially inward facing surface and a radially outward facing surface, the radially inward facing surface defining an opening configured for being disposed adjacent the patient's nasal openings, and the radially outward facing surface defining an exhalation port,
  wherein the partially toroidal body comprises a first end and a second end,
  wherein each of the first and second ends define openings that are in fluid communication with the opening defined by the radially inward facing surface, the exhalation port, and a channel that extends between the first and second ends of the nasal mask;
  wherein the openings defined by the first and second end are couplable to an air supply source, and exhalation through the patient's nose passes through the exhalation port; and
  wherein the nasal mask defines the at least one recessed portion on an outwardly facing surface of the body of the nasal mask, the at least one recessed portion configured for receiving the at least one post of the air delivery device frame for at least partially coupling the air delivery device frame to the nasal mask,
 a $CO_2$ concentration sensor coupled to the sensor frame; and
 a processor electrically coupled to the $CO_2$ concentration sensor and a memory, the memory having computer-executable instructions stored thereon that, when executed by the processor, cause the processor to:
  receive a $CO_2$ concentration signal from the $CO_2$ concentration sensor corresponding to a $CO_2$ concentration in a gas exhaled by the patient,
  determine, based on the $CO_2$ concentration signal, if the $CO_2$ concentration received by the $CO_2$ concentration sensor is less than a minimum threshold of $CO_2$ concentration expected for the gas exhaled, and
  generate an alarm signal in response to the $CO_2$ concentration being less than the minimum threshold of $CO_2$ concentration,
 wherein the sensor frame aligns the $CO_2$ concentration sensor with the at least one of the patient's air passages and/or an exhalation passage from the air delivery device when the air delivery device is in an intended position relative to at least one of the patient's air passages.

7. The CPAP system of claim 6, further comprising a power source electrically coupled to the processor.

8. The CPAP system of claim 6, further comprising an alarm generator, wherein the alarm generator is electrically coupled to the processor and generates an alarm in response to receiving the alarm signal from the processor.

9. The CPAP system of claim 8, wherein the alarm generator is a piezo-buzzer, an audible alarm, and/or a haptic actuator.

10. The CPAP system of claim 8, wherein the alarm generator generates an alarm at a predetermined time interval after the $CO_2$ concentration detected by the $CO_2$ concentration sensor falls below the threshold.

11. The CPAP system of 10, wherein the predetermined time interval is five seconds.

12. The CPAP system of claim 6, wherein the nasal mask defines the at least one recessed portion, and the air delivery device frame comprises the at least one post for engaging the recessed portion.

13. The CPAP system of claim 6, further comprising at least one air supply tube, wherein one end of the at least one air supply tube is coupled to the opening of the first end or the second end of the nasal mask, and the other end of the at least one air supply tube is coupled to an air source.

* * * * *